(12) United States Patent
Mason (10) Patent No.: US 8,505,388 B2
(45) Date of Patent: Aug. 13, 2013

(54) APPARATUS AND METHOD FOR SIMULATING LIFETIME OF AND/OR STRESS EXPERIENCED BY A ROTOR BLADE AND ROTOR DISC FIXTURE (75) Inventor: Paul J Mason, Ashbourne (GB)

(73) Assignee: Rolls-Royce, PLC, London (GB)

(*) Notice: Subject to any disclaimer, the term of this patent is extended or adjusted under 35 U.S.C. 154(b) by 540 days.

(21) Appl. No.: 12/710,882

(22) Filed: Feb. 23, 2010

(65) Prior Publication Data
US 2010/0263453 A1 Oct. 21, 2010

(30) Foreign Application Priority Data

Apr. 15, 2009 (GB) .................................. 0906342.1

(51) Int. Cl.
G01N 3/08 (2006.01)
(52) U.S. Cl.
USPC ............................................................ 73/826
(58) Field of Classification Search
USPC ............................................................ 73/826
See application file for complete search history.

(56) References Cited

U.S. PATENT DOCUMENTS

| | | | | |
|---|---|---|---|---|
| 2,948,505 A * | 8/1960 | Sonder | ..................... | 416/96 R |
| 3,603,143 A | 9/1971 | Detert et al. | | |
| 3,690,160 A | 9/1972 | Kriesten | | |
| 3,802,255 A * | 4/1974 | Struthers et al. | ................. | 73/856 |
| 4,022,545 A | 5/1977 | Shank | ........................... | 416/221 |
| 5,314,307 A * | 5/1994 | Farmer | ............................. | 416/2 |
| 5,741,119 A * | 4/1998 | Heppenstall | .............. | 416/219 R |
| 6,183,202 B1 * | 2/2001 | Ganshaw | ................... | 416/219 R |
| 6,250,166 B1 | 6/2001 | Dingwell et al. | | |
| 6,561,764 B1 * | 5/2003 | Tiemann | ..................... | 416/96 R |
| 6,718,833 B2 | 4/2004 | Xie et al. | | |
| 6,773,234 B2 * | 8/2004 | Sinha et al. | ................ | 416/219 R |
| 6,832,896 B1 * | 12/2004 | Goga et al. | ..................... | 416/191 |
| 7,204,153 B2 * | 4/2007 | Phipps | ............................ | 73/808 |
| 7,874,806 B2 * | 1/2011 | Phipps | ..................... | 416/219 R |
| 2005/0252304 A1 | 11/2005 | Woodward et al. | | |

FOREIGN PATENT DOCUMENTS

| | | |
|---|---|---|
| EP | 1 598 655 A2 | 11/2005 |
| EP | 1 602 914 A2 | 12/2005 |
| KR | 2003-0017044 | 3/2003 |
| RU | 2 196 313 C2 | 1/2003 |

OTHER PUBLICATIONS

Great Britain Search Report issued on Jul. 1, 2009 in Great Britain Patent Application No. GB0906342.1.

* cited by examiner

Primary Examiner — Lisa Caputo
Assistant Examiner — Octavia D. Hollington
(74) Attorney, Agent, or Firm — Oliff & Berridge, PLC (57) ABSTRACT An apparatus for simulating stresses experienced by a rotor blade root in a complementary disc fixture, especially in gas turbine engines. The apparatus comprises a mounting member for receiving a blade speciman having a root. The mounting member has an aperture for receiving the root of the blade specimen, and blade contacting regions on either side of said aperture for holding said blade specimen in said aperture. The apparatus further comprises an actuator for applying a tension load to said blade specimen. The blade contacting regions are undercut such that there is a gap between said blade contacting regions and a main body of said mounting member, whereby the blade contacting regions are able to deflect outward into said gap when a tension load is applied to the blade specimen.

25 Claims, 4 Drawing Sheets

APPARATUS AND METHOD FOR SIMULATING LIFETIME OF AND/OR STRESS EXPERIENCED BY A ROTOR BLADE AND ROTOR DISC FIXTURE

FIELD OF THE INVENTION

The present invention relates to fatigue testing of materials and more particularly relates to an apparatus and method for simulating fatigue of rotor blade roots in complementary rotor blade slots. The method and apparatus may simulate the lifetime of, and stresses experienced by, a rotor blade and rotor disc fixture. The invention will find particular application to rotor blade and disc fixtures in a gas turbine engine, but may also be applied to other apparatus with rotating blades. For example, it may be used to simulate blade fixing arrangements in a compressor, a turbine, a rotor craft, a wind turbine or windmill.

It is necessary to fatigue test the fixing arrangement of the rotor blade to ensure that its operational lifetime and resistance to stress meets the desired requirements. However, because of the large and variable forces involved, it is difficult to test a blade root under conditions representative of the operating conditions in a gas turbine engine. It has been found to be desirable to avoid altering critical parts of architecture of the tested component away from the architecture of the component as used as test results may be affected.

It is also desirable to avoid having complex and expensive test equipment, with multiple actuators for applying different loads and which can cause long test times due to the response time of the actuators. Long tests are undesirable and can result in the inability to carry out testing of multiple design options, which have the potential to result in design improvements. It has also been found to be desirable to provide test architecture that is easily adaptable to different blade sizes and designs.

Representative tests can be performed using slices of a blade with the slice used usually being the one subjected to the highest stress. However, although slice testing is useful it does not always give a correct estimate of the LCF as the slice does not give the same readings as that of a whole blade in operation. On the other hand, whole blade static testing is difficult as there is a need to apply many tens of tonnes of force (30 to 60 being typical) to give a representative loading under operation. There is a difficulty in applying sufficient force to the whole blade and difficulty in applying sideways or non-axial loads.

SUMMARY OF THE INVENTION

A first aspect of the present invention provides an apparatus for simulating the stresses experienced by a mounting arrangement of a rotor blade in a rotor disc, the apparatus comprising: —a mounting member for receiving a blade specimen having a root;

said mounting member having an aperture for receiving the root of the blade specimen, and blade contacting regions on either side of said aperture for holding said blade specimen in said aperture, said blade contacting regions being undercut such that there is a gap between said blade contacting regions and a main body of said mounting member, whereby the blade contacting regions are able to deflect outward into said gap (and towards the main body) when a tension load is applied to said blade specimen; and an actuator for applying a tension load to said blade specimen.

The apparatus may be used for simulating the stresses experienced by blade mounting arrangements for any suitable apparatus with rotating blades, eg a gas turbine engine, a compressor, a turbine, a rotor craft, a wind turbine or windmill.

A blade specimen may be mounted to the mounting member and a tension load applied in order to simulate the operation stress experienced by the blade. The gap between the contacting regions and the main body of the block enables the blade contacting regions to deflect outward in a way which simulates the strain (change of shape) of the rotor disc when rotating in operating conditions.

Stress analysis may be used to design the mounting member such that the slippage, deformation and strain match those in operation of the simulated rotor apparatus. This can be confirmed by using strain indicators, such as strain gauges, and/or pressure or colour contact films and testing the mounting member against a load for one or more cycles.

The blade specimen may simulate a whole rotor blade across its chord, or a section or slice of a rotor blade. It may be convenient to select a slice of the rotor blade which experiences maximum stress during operation and make blade specimen corresponding to said slice of the blade. By simulating only a slice, it is possible to reduce the force applied by the actuator while still achieving the desired stress conditions.

The rotor blade contacting regions are preferably designed to match the root of the blade specimen. They preferably provide a friction fit, for example a dovetail or fir tree root arrangement.

Preferably said aperture and said gap between the main body and the blade contacting regions form a single recess when no blade is mounted in the aperture. Preferably said gap has a similar order of thickness to the thickness of the blade contacting region.

Preferably the mounting member has a pair of blade contacting regions each having a respective contact face for contacting the root of a blade specimen, said contact faces being designed to match the profile of the root of the blade specimen.

Preferably the apparatus has one or more regulating members, eg bolts or screws, for regulating stiffness of the mounting member.

Preferably the actuator is arranged for cycling the load. Cycling means repeatedly varying the load between at least two values. For example the cycling may be between 10% and 100% of maximum load at 5 Hz; however, these values are given as an example only and the present invention is not limited to this.

Preferably the apparatus has only a single actuator for applying a load to the blade specimen; i.e. there is not more than one actuator for applying a load to the blade specimen.

The apparatus may comprise a test rig having a base for supporting the mounting member and an arrangement (eg a yoke) for attaching to the blade specimen to an actuator. A tension load may be applied to the blade specimen by using the actuator to apply a force separating the mounting member and blade specimen attachment member.

A second aspect of the present invention provides a method of simulating the stresses experienced by a mounting arrangement of a rotor blade in a rotor disc, comprising the steps of placing a blade specimen having a root in a mounting member for receiving the blade specimen, said mounting member having an aperture for receiving the root of the blade specimen, and blade contacting regions on either side of said aperture for holding said blade specimen in said aperture, said blade contacting regions being undercut such that there is a gap between said blade contacting regions and a main body of said mounting member, whereby the blade contacting regions are able to deflect outward into said gap (and towards the main body) when a tension load is applied to said blade specimen; and using an actuator to apply a tension load to said blade specimen.

The method may be used to simulate the life of blade mounting features in any suitable apparatus with rotating blades, eg a gas turbine engine, a compressor, a turbine, a rotor craft, a wind turbine or windmill. Further, the method may use an apparatus having any of the features of the first aspect of the invention discussed above.

The method may further comprise the step of regulating the stiffness of the mounting member by adjusting one or more regulating members, eg bolts extending through the main body of the mounting member.

The method may comprise the steps of providing a base for supporting the mounting member, attaching the blade specimen to the actuator and using said actuator to apply a tension load to the blade specimen.

The load applied to the blade specimen is preferably cycled. Preferably only a single actuator is used for applying a load to the blade specimen (i.e. preferably not more than one actuator is used for this purpose). This provides a solution which is simple and reliable and which may reduce costs compared to some prior art methods. The method may comprise the step of checking strain indicators applied to the blade specimen and/or the blade mounting member to confirm that stresses are at the desired level. The method may comprise the step of adjusting the load until a desired strain is achieved (eg by reference to the strain indicators).

A third aspect of the present invention provides an apparatus for simulating the axial and radial stresses experienced by the root and shank of a rotor blade when the rotor blade is in operation; the apparatus comprising: —a blade mounting member mounted to a base and adapted to receive and hold the root of a blade specimen; a blade attachment member for attaching to a wing portion of a blade specimen; an actuator for applying a force separating the blade mounting member and blade attachment member so as to apply a tension load to a blade specimen when a blade specimen is mounted to the blade mounting member and attached to the blade attachment member; characterised in that; one or both of the blade attachment member and blade mounting member is movable relative to the other in a manner such that the lean and/or twist of a blade specimen mounted to the blade mounting member and attached to the blade attachment member is adjustable.

The above arrangement makes it possible to provide the desired axial and radial stress for the blade root and shank when the actuator applies a tension load. Furthermore this may be achieved with a single actuator (i.e. the apparatus may have only a single actuator for loading the blade), rather than by using several different actuators to provide loads in different directions. The blade specimen in this third aspect of the present invention is preferably a specimen representative of the whole blade along its chord, but may alternatively represent only a slice of the blade (in which case the thickness of the blade mounting member can be made thinner also). The blade specimen comprises a root, a shank and a wing or aerofoil portion. While it would be possible for the blade specimen to have a full wing corresponding to the length of the blade being simulated, more usually the blade specimen will be cut short and have only a part of the wing in order that the apparatus can be made smaller. The blade mounting member may have any of the features of the mounting member of the first and second aspects of the present invention.

The apparatus may have x, y and z axes, the actuator being arranged for applying a load along the z axis and at least one of the blade attachment member and blade mounting member being movable relative to the other in the x and/or y directions. The x and y directions are defined as any directions perpendicular to the z axis.

The apparatus may have first and second opposing structural members, preferably in the form of plates. The blade mounting member may be mounted to the first structural member either directly or indirectly (eg via a movable rack which is mounted to the first structural member). The blade mounting member is preferably movable in a plane substantially parallel to the plane of the first structural member. The blade attachment member may be supported by the second structural member, eg it may be attachable (directly or indirectly) to an actuator which is mounted to the second structural member. This makes it easy to adjust the lean of the blade by moving the blade mounting member back and forth in a line parallel to faces of the blade specimen when it is mounted in the blade mounting member. For example, the blade mounting member may be mounted to the first structural member via one or more rails or recesses and movable along said rails or recesses. The blade mounting member may be movable relative to the first structural member in one direction (eg along the y axis) or in two directions (eg along the x and y axes). The twist of the blade specimen may be adjusted by a combination of displacement in the x and y directions. The position may be temporarily fixable by locking the blade mounting member in place. Preferably the way in which the blade attachment member is supported by the second structural member or actuator provides a degree of play to allow a desired level of non axi-symmetric loading.

In alternative embodiments it would be possible for the blade attachment member to be movable instead of, or in addition to, the blade mounting member. Further it would be possible for twist to be applied by applying a torque to the blade mounting member via the actuator.

Preferably the actuator is mounted to the second structural member and a blade receiving part of the blade mounting member is offset along the x and/or y axis relative to the actuator.

The blade mounting member (200) may have any of the features of the first aspect of the present invention.

Strain indicators (eg strain gauges or a pressure or colour contact film) may be applied to the blade mounting block and/or the blade itself (in particular the root and/or shank of the blade). They strain indicators may be used to confirm that the contact and shank stresses experienced in the apparatus are representative of the strain experienced in operation of the simulated rotor apparatus (eg as given by full strain gauge engine test results).

Preferably a link between the blade attachment member (400) and the actuator (390) has a degree of play to allow non axi-symmetric loading. The blade attachment member may be provided with a part for attachment to the second structural member. For example, the part for attachment may be an eyelet through which a bolt or other member can be used to attach or mount the eyelet to the second structural member. The position of said part for attachment can be adjusted in order to fine tune its position in relation to a central axis of the blade attachment member. The ability to fine tune the load position (the position of attachment to the second structural member) helps to match the strain gauge readings in the shank region of the blade against those of a full test engine and so remove any F.E. Analysis inaccuracies.

Preferably the actuator is arranged to cycle the loading, as discussed above in the other aspects of the invention (eg from 10%-100% of full load at 5 Hz, but other values will be possible and apparent to a person skilled in the art depending upon the system being modelled).

A fourth aspect of the present invention provides a method of simulating the axial and radial stresses experienced by the root and shank of a rotor blade when the rotor blade is in operation; the method comprising the steps of: providing a blade mounting member adapted to receive and hold the root of a blade specimen; providing a blade attachment member which is adapted for attachment to the wing of a blade specimen; mounting the root of a blade specimen in the blade mounting member and attaching a wing of the blade specimen to the blade attachment member; adjusting the relative positioning of the blade mounting member and the blade attachment member in order to achieve a desired lean and twist of said blade specimen, and using an actuator to apply a force to the first and/or second structural member so as to apply a tension load to said blade specimen.

Adjusting the relative position of the blade mounting member and the blade attachment member provides the desired axial and radial stress for the blade root and shank when the actuator applies a tension load. Optionally the relative position of the blade attachment member and blade mounting member may be fixed prior to applying the load, eg by using a locking device to fix the position of one or both members.

Preferably the load is applied by only one actuator.

The method may further comprise the step of regulating the stiffness of the blade mounting member by adjusting one or more regulating members. The regulating members may extend through the main body of the mounting member.

The method may further comprise the steps of checking strain indicators (eg strain gauges or a pressure or colour contact film) applied to the blade specimen (especially the root and shank) and/or the blade mounting member. Readings from the strain indicators may be used to confirm that the contact and shank stresses are at a desired level, eg representative of the full strain gauge engine test results.

The method may further comprise the step of adjusting the load and/or blade mounting member position and/or blade attachment member position until a desired strain is achieved. The strain may be measured by a strain indicator. Further adjustment of the load may be carried out when necessary during the fatigue testing.

The blade attachment member may be provided with a part for attachment to the second structural member and the method may comprise the step of adjusting the position of said part to a selected position. The position of the part can be adjusted in order to fine tune its position in relation to a central axis of the blade attachment member.

Preferably the load applied to the blade is cycled between predetermined values (eg 10%-100%) at a frequency for a certain period of time in order to simulate the life the blade mounting arrangement. Preferably the axial and radial stresses are applied by a single actuator, rather than using separate actuators for each direction of stress.

The fourth aspect of the invention may incorporate any of the features of the third aspect of the present invention.

Any features of the above aspects of the invention may be combined together.

BRIEF DESCRIPTION OF THE DRAWINGS

Embodiments of the invention will now be described by way of example with reference to the accompanying drawings in which.

DETAILED DESCRIPTION

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

First Embodiment

An apparatus and method for simulating the stresses experienced by and/or the life of a mounting arrangement of a rotor blade in a rotor disc will now be described. The mounting arrangement refers to the features attaching the blade root to the rotor disc and includes both the root of the blade and the mounting features of the rotor disk. The method and apparatus will be particularly useful for simulating a blade mounting arrangement in a gas turbine engine. However it may be used to simulate blade mounting arrangements in any suitable apparatus with rotating blades, eg a compressor, a turbine, a rotor craft, or wind turbine.

In the present embodiment the root of the rotor blade under investigation forms a dovetail fit with the rotor disc. However arrangements with other friction fits, eg a fir tree root arrangement, could also be simulated.

Figure 1:
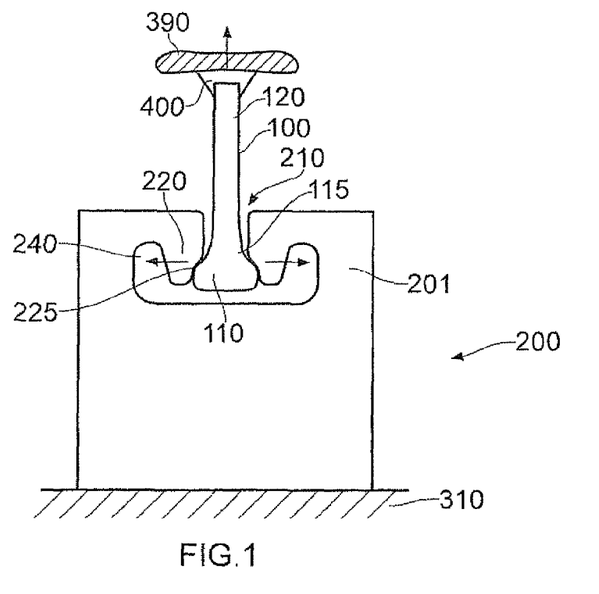
FIG. 1 is a cross sectional view of a blade specimen and blade mounting member according to a first embodiment of the present invention.

The apparatus is used to simulate the rotor blade root region stress distribution, displacements and slip generated by the cycle frequency load. FIG. 1 shows a cross-sectional view of a blade specimen 100 mounted in an apparatus 200.

In the first embodiment of the present invention the blade specimen 100 is a specimen with a root 110 and shank 115 geometry which is representative of the root and shank region of the blade being simulated. The root of a blade is the part which contacts the disc fixture and the shank is a fillet connecting the root to regions of the blade above the root.

In the first embodiment the blade specimen 100 simulates a slice of a blade, eg the slice which experiences the greatest stresses in use. The thickness of the blade specimen is thus less than the actual blade as only a slice is simulated. However the thickness (in the direction extending along the blade chord) should be sufficient to prevent edge effects from influencing the test results. However, the invention is not limited to modelling a blade slice and it would be possible for the specimen to model the whole blade across its chord. In this case the blade specimen will have a thickness similar to the blade being modelled. It would also be possible to place a whole blade including the aerofoil in the apparatus, although this would greatly increase the necessary size of the apparatus.

The blade specimen can either be metallic or composite depending on the application. The contact regions 115 of the blade specimen are machined to produce contact regions which are representative of the full blade. That is, the profile of the blade specimen root 110 mirrors the profile of the root of the simulated blade.

The apparatus comprises a mounting member 200 in which a root 110 of the blade specimen 100 may be mounted as shown in FIG. 1. There is also an actuator 390 for applying a tension load to the blade specimen 100. The mounting member 200 comprises a block having a main body 201 and an aperture 210. The block has blade contacting regions 220 on either side of the aperture 210. The blade contacting regions 220 have a profile matching the profile of contact regions 115 of the root 110 of the blade specimen 100, eg in a dovetail fit. The blade contacting regions 220 of the mounting member act to receive and hold the blade specimen in the aperture 210 by a friction fit. The mounting member 200 and in particular the blade contacting regions 220 are designed by stress analysis so that they displace in such a way that the desired conditions (simulating the rotor apparatus in operation) will be produced.

As shown in FIG. 1 the blade contacting regions 220 are undercut so that there is a gap 240 between the blade contacting regions 220 and a main body 201 the block. This enables the blade contacting regions (or lobes) to deflect radially outwards into the gap (and towards the main body 201 of the block), when a tension load is applied to the blade specimen 201. Without the gap 240 any deflection would be up and outwards (to the left or right of FIG. 1), but having the gap 240 allows a greater component of deflection outwards to the right or left and so more closely represents the behaviour or an actual disc component in a turbine.

In this way control of the contact stresses, displacement and slip may be achieved. In particular the mounting member 200 and blade contacting regions 220 are designed such that the displacement, slip and contact stresses are similar to those seen in service of the simulated rotor and rotor disc arrangement.

In this embodiment there are two opposing blade contacting regions 220 each with contact faces 225. The contact faces match the adjacent surfaces of the root of the blade specimen 110. The deflection of the blade contacting regions 220 helps to keep the stress on the blade root 110 close to that seen in service. FIG. 2a shows the mounting member 200 by itself without an inserted blade specimen. It can be seen that the aperture 210 joins with the gaps 240 to form a single recess in the block 200. It is preferred that each gap 240 has a similar width (in the direction left to right of FIG. 1) to the width of the blade contacting region 220 which it undercuts. This helps to achieve stress distributions representative of those experienced by a blade root in operation. The shape of the undercut 240 is specific to the blade design and load range being tested. It may be designed by or with the help of an iterative process involving many runs using finite element analysis.

The mounting member 200 (which simulates the 'disc fixture') will typically be metallic, being manufactured from the same material as the simulated disc or from an alternative material with shims over the contact region. The shims will be of a material which is representative of the disc. The blade specimen thickness should be enough to reduce the 'edge effects' to a level where by they do not influence the contact or fillet stresses. While shims are not essential, they help prevent unrepresentative coefficients of friction between the mounting member 200 fixture and the blade specimen 100.

The mounting member 200 may be mounted on a base 310. The distance between the blade contacting regions 220 and the part of the mounting member 200 which is mounted to the base 310 should be suitably long so as to allow the loading effect of the rig attachment at the bottom of the mounting member 200 to be washed out by the contact region.

An actuator 390 is connected to an upper part 120 of the blade specimen, eg via a yoke or other attachment arrangement 400. The upper part 120 of the blade specimen is remote from the root of the blade specimen 110. The actuator 390 is used to apply a tension load to the blade specimen as shown in FIG. 1. While in the present embodiment the actuator is at the top of the blade specimen and the base 310 holds the mounting member 200 in place, it would in theory be possible for the top of the blade specimen to be held by a support while an actuator applied a tension load to the base.

In order to simulate the stresses experienced by the mounting arrangement and conduct fatigue testing, the blade specimen 100 is mounted as described above and then the actuator 390 is used to cycle the load until the desired cyclic life has been achieved. If faults, cracks or other failures occur during this period then they are noted and may indicate that the design does not have the desired cyclic life. 'Cycling' means varying the load applied. The cycling may, for example, be between 10% and 100% of a predetermined maximum load, but other values may be used depending on the application. The load cycling can be at any suitable rate depending on the application and operating conditions being simulated. For example, about 5 Hz may be appropriate, in which case the root arrangement can be cycled about 100,000 times in about a day. This compares to about a year for some conventional prior art test methods that involve cycling a set of blades on a rotating drum.

If the blade specimen simulates a blade slice, then its response should be representative of the simulated region of the blade (eg the worst fatigue location) and this information can be used for design purposes. If the blade specimen simulates a whole blade then the life of the blade may be predicted. It is important that the mounting member 200 and blade specimen root 110 experience stresses, slip and displacement similar to that experienced by the simulated rotor blade and rotor disc in operating conditions. The application of a tension load to the blade simulates the centripetal load experienced by a rotor in operation. Further, in the present invention, the blade contacting portions 220 of the mounting member 200 are designed to deflect in a way which simulates the deformation caused by the centripetal force of rotation of the disc and the contact stresses applied by the rotor in operation. In some prior art methods the deformation and stresses were simulated by changing the shape of a blade slice root from the actual design in order to give stresses and deformation similar consistent with those seen in operation. In contrast in the present invention it is preferred that the root 110 of the blade specimen 100 has a profile mirroring that of the simulated rotor blade and any adjustments are made to the mounting member 200.

Figure 2:
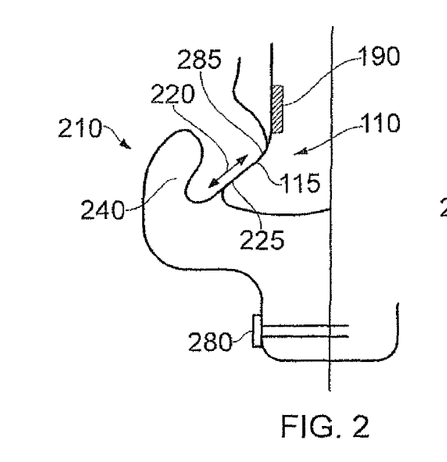
FIG. 2 is a detailed partial cross sectional of a blade specimen and blade mounting member according to a first embodiment of the present invention.
Figure 2A:
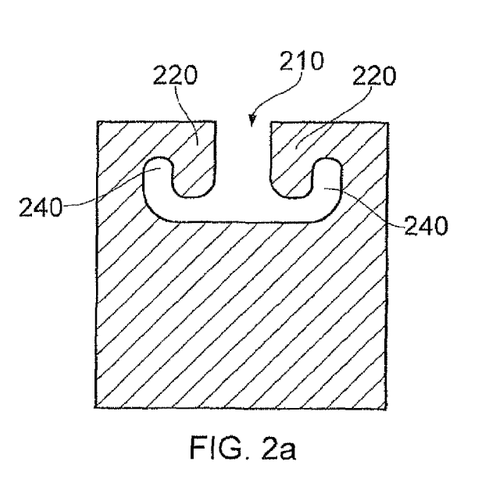
FIG. 2a shows the blade mounting member 200 of FIG. 2 by itself without an inserted blade specimen.

FIG. 2 shows a cross section of part of the blade specimen 100 and mounting member 200 in detail. The slippage, deformation and stresses experienced by the mounting member 200 are determined by, inter-alia, the material used, the profile of the blade contacting regions 220, the gap 240 undercutting the blade contacting regions and regulating members 280. FIG. 2 shows the dovetail fit between the contact portion 115 of the root 110 of the blade specimen and a blade contacting region 220 of the mounting member 200. The point of maximum stress 285 and the possible slippage between the blade contacting region and the blade root and the possible deflection of the blade contacting region are also shown. One or more regulating members 280 are used to regulate the stiffness of the mounting member. eg the regulating members 280 may be in the form of bolts or the like and extend through one or more holes 270 in the mounting member 200. The holes 270 are preferably in walls of the main body of the block 200 and extend through to a recess 260 directly below the aperture 210. As shown in FIG. 2 there are two pairs of opposing holes 270, although the present invention is not limited to that number. By placing a regulating member 280, eg a bolt, through each hole pair 270 and tightening, the stiffness of the mounting member 200 can be regulated.

The application of bolts or the like requires that the mounting member has a certain thickness. If the blade specimen is thin then the mounting member may also be thin and the above arrangement may not be suitable. An alternative arrangement for regulating the stiffness using a different type of regulating member may be used. For example, the regulating member could be restraining blocks on the outside of the mounting member 200, which are capable of being moved up or down to control stiffness. Strain indicators 190, eg strain gauges and/or pressure or colour contact films may be applied to the blade contacting regions 220 and/or the root and/or shank of the blade specimen in order to confirm that the experienced stresses and strain are at the desired level (eg similar to those experienced in operation of the rotor system being simulated). When the mounting member 200 is designed and manufactured for the first time, it may be tested to see if it gives the desired response, by applying one or more cycles of a representative test load and observing the strain indicators. When the mounting member is being used in the apparatus together with a blade specimen, to test a specific mounting arrangement, strain indicators may likewise be used to check that the desired conditions are achieved during the test.

Second Embodiment

Figure 3:
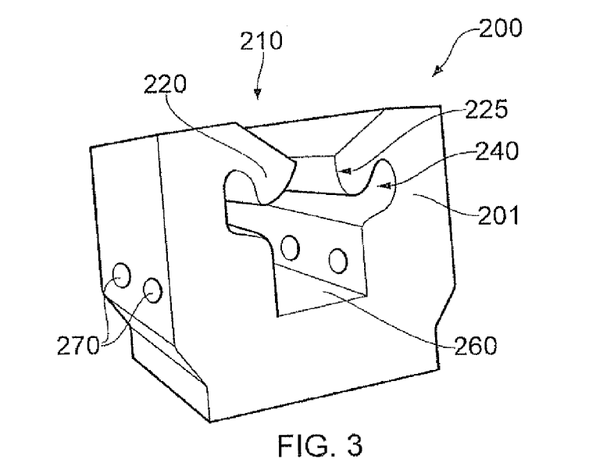
FIG. 3 is a perspective view of a mounting block which may be used in the first and second embodiments of the present invention.
Figure 4:
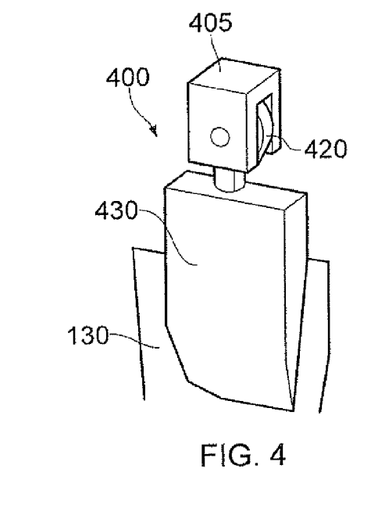
FIG. 4 shows the top part of a rotor blade attached to a blade attachment member of an apparatus according to a second embodiment of the present invention.
Figure 5:
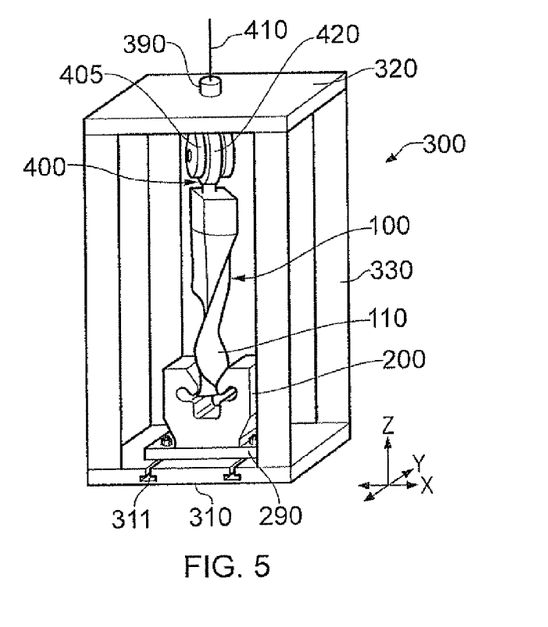
FIG. 5 shows a testing apparatus for testing a blade specimen according to a second embodiment of the present invention.

FIGS. 3 to 5 show an apparatus which may be used for testing a rotor blade specimen in a static fatigue rig. The apparatus is able to replicate the displacement and stresses in the root and shank region of the blade both in the radial and axial directions.

A blade mounting member 200 is designed to reproduce the root (eg dovetail) contact and shank stresses, slip and displacement observed in the simulated rotor blade and rotor disc mounting arrangement in operational conditions (eg those in a turbine engine under centripetal loading). A tension load simulating the centripetal load is applied to the rotor blade specimen 100 through a blade attachment member 400 attached to the wing (eg the aerofoil region) of the blade specimen. The tension load is applied in a way that allows non axi-symmetric loading and so the introduction of blade lean and twist. Lean and twist are required to replicate the change in blade shape under the centripetal loading and steady aerodynamic forcing at redline speed. Application of non axi-symmetric loading and/or causing the blade to lean and twist helps to provide the correct load distribution and so stress in the root and shank regions of the blade.

FIG. 3 shows a blade mounting member 200 in detail. The blade mounting member 200 shown in FIGS. 3 and 5 is similar to the blade mounting described above in the first embodiment. In particular it has undercut blade contacting regions 220 surrounding an aperture 210. The blade contacting regions are undercut to provide a gap 240 between the blade contacting region 220 and the main body 201. This allows the blade contacting regions to deflect outwards into the gap when a tension load is applied to the blade specimen 100. The blade mounting member also has a plurality of holes 270 for receiving regulating members 280 (eg bolts) extending through the mounting member 200. The regulating members 280 may be tightened or adjusted in order to regulate the stiffness and bulk displacement of the blade mounting member 200 under load. The blade mounting member shown in FIGS. 3 and 5 differs from the blade mounting member shown in FIG. 1 in that it has greater thickness as it is designed to receive and support a blade specimen having a thickness corresponding to a whole blade along its chord, rather than just a blade slice. However, it would be possible to modify the blade mounting member shown in FIGS. 3 and 5 for use with a blade specimen corresponding to a blade slice by making the blade mounting member thinner.

While the second embodiment preferably uses a blade mounting member as shown in FIGS. 3 and 5, it would be possible instead to use a conventional blade mounting member with no undercut gap 240. While the undercut gap has the advantages described above in the first embodiment, a principal advantage of the second embodiment is the ability to simulate stresses arising due to lean and twist of the blade, as will be discussed in more detail below.

FIG. 4 shows a blade attachment member 400 for attaching to the top of the wing 130 of the blade specimen 100. The blade attachment member 400 comprises two blade receiving parts 430 which between them receive the wing of the blade 100. Each blade receiving part has a face that matches either the suction or pressure side of the wing (eg aerofoil) so that when the two blade receiving parts 430 of the blade attachment member are brought together the wing 130 is securely held between them. The blade attachment member may be secured to the blade specimen by adhesive or mechanically (eg putting one or more bolts through the attachment member and blade wing), but it is preferable to use both adhesive and a mechanical method. The blade mounting member 200 and blade attachment member 400 are placed in a test rig 300 as shown in FIG. 5. The test rig comprises first 310 and second 320 opposing structural members which form parallel plates. The structural members 310, 320 are separated by support legs 330 extending between the two members. The test rig is capable of applying the required tensile load to the blade specimen 100 through a single actuator 390. The blade mounting member 200 and the blade attachment member 400 are mounted to the test rig in such a way that their relative positioning may be adjusted in order to introduce the desired twist and/or lean to the blade specimen 100. In this way twist, lean and non axi-symmetric loading may be simulated with only a single actuator. The test rig has x, y and z axes as shown in FIG. 5. The z axis is the axis along which the actuator acts.

The preferred manner in which the blade mounting member 200 and the blade attachment member 400 are mounted to the test rig will now be described. The blade mounting member 200 is mounted directly or indirectly to the first structural member 310. It is mounted in such a way that it can be moved in a plane parallel to the plane of the first structural member. The test rig may have a locking mechanism for temporarily fixing the blade mounting member 200 in a selected position. In the illustrated example the blade mounting member 200 is mounted indirectly via a base plate 290. The base plate 290 is mounted to first structural member 310 by protruding parts which extend into elongate recesses 311 extending across the first structural member. The blade mounting member 200 can thus be slid in the y-direction across the structural member 310 along the path of the recesses 311. This allows for non axi-symmetric loading and makes it possible to give the blade 100 a desired 'lean' in order to simulate operating conditions. Furthermore the blade mounting member 200 is offset laterally in the x-direction relative to the actuator 390, i.e. the centre of the blade receiving recess 210 is offset relative to the axis 410 of the actuator 390. This offset in the x-direction may be fixed or adjustable and together with the adjustable offset in the y-direction provides the desired twist to the blade. In alternative embodiments the position of the blade attachment member 400 may be adjustable along the x and/or y axes.

The blade attachment member 400 is attached to the test rig in such a way that there is a degree of play which allows for non axi-symmetric loading. In particular it can accommodate movement of the blade mounting member relative to the blade attachment member when a blade specimen is held between the two.

In the arrangement shown in FIGS. 3 to 5 the blade attachment member 400 comprises the blade receiving members 430 and a part for attachment 420. The part for attachment 420 is secured to the blade receiving parts 430 and preferably is integrally formed therewith because of the significant load it must bear. The part for attachment 420 is preferably an eyelet which is attachable to a block 405, for example by a bolt or other elongate member. The block 405 is fixed to the actuator 390. The actuator 390 is mounted to the second structural member 320 of the test rig 300. Thus the second structural member (indirectly) supports the blade attachment member 400. The eyelet provides the desired degree of play when the blade mounting member 200 is moved relative to the blade attachment member 400.

In the illustrated embodiment, shown in FIG. 4, the part for attachment 420 is positioned on a central axis of the blade attachment member 400. Alternatively it could be offset from the central axis to either side (eg to the left or right in FIG. 4) in order to facilitate non axi-symmetric loading and lean and twist of the blade specimen. If the part for attachment 420 is not integrally formed with the blade receiving parts 430, then it may be arranged in such a way that its position relative to the blade receiving parts is adjustable. For example, it may be possible to slide the part for attachment 420 along the top of the blade receiving parts 430 in order to fine tune its position in relation to a central axis of the blade and/or blade attachment member. The ability to fine tune the load position provides the ability to match the strain gauge readings in the shank region of the blade against those of a full test engine and so remove any F.E. Analysis inaccuracies.

The actuator 390 is mounted to the second structural member 320 and attached to the blade attachment member 400. The actuator 390 is arranged to apply a force separating the blade attachment member 400 from the blade mounting member 200. In alternative embodiments it would in theory be possible to have the actuator mounted to the first structural member and arranged to apply force to the blade mounting member instead. In another alternative arrangement it would be possible to design the actuator so that it applied a torque to the blade in order to provide the desired twist, however applying twist by adjusting the position of the blade mounting member is currently preferred.

Strain indicators may be applied to the blade root and shank and/or the blade mounting block in order to confirm that the contact and shank stresses and slip are representative of the simulated operating conditions.

Figure 6:
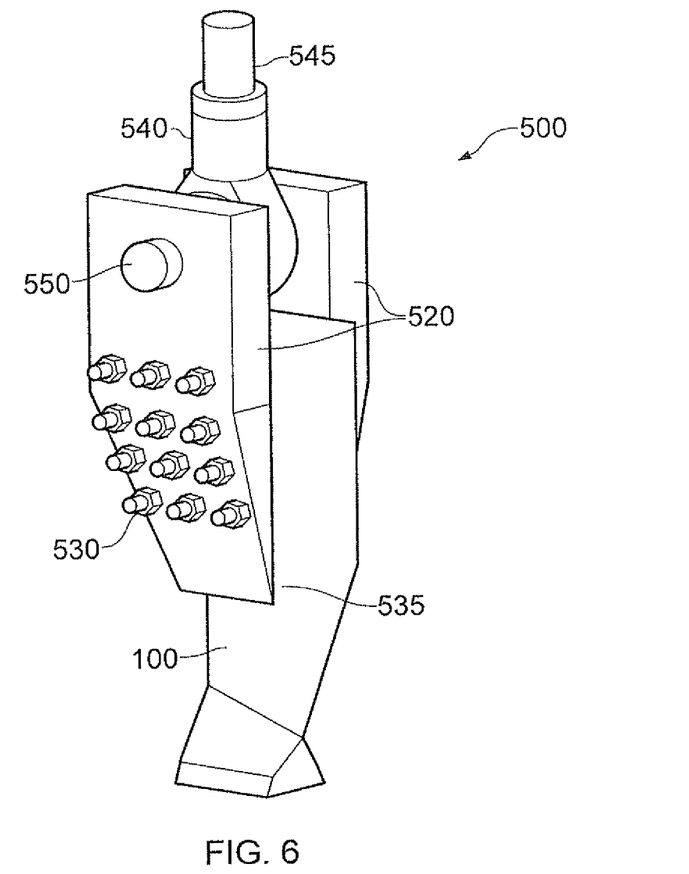
FIG. 6 shows an alternative design of blade attachment member holding a blade specimen.

FIG. 6 shows an alternative blade attachment member 500. The blade attachment member 500 comprises a pair of blade receiving members 520 for receiving a wing of the blade specimen 100. The blade specimen wing may be attached to the blade receiving members by bolts 530 and/or adhesive 535, preferably both. An adaptor 540 attaches the blade attachment member 500 to the actuator 390. The adaptor 540 has a threaded portion 545 which may be screwed into the actuator 390. The other end of the adaptor has an eyelet for receiving an elongate member 550 which extends through apertures 525 in the blade receiving members 520. This arrangement provides the desired degree of play between the actuator 390 and the blade attachment member 500.

Figure 7:
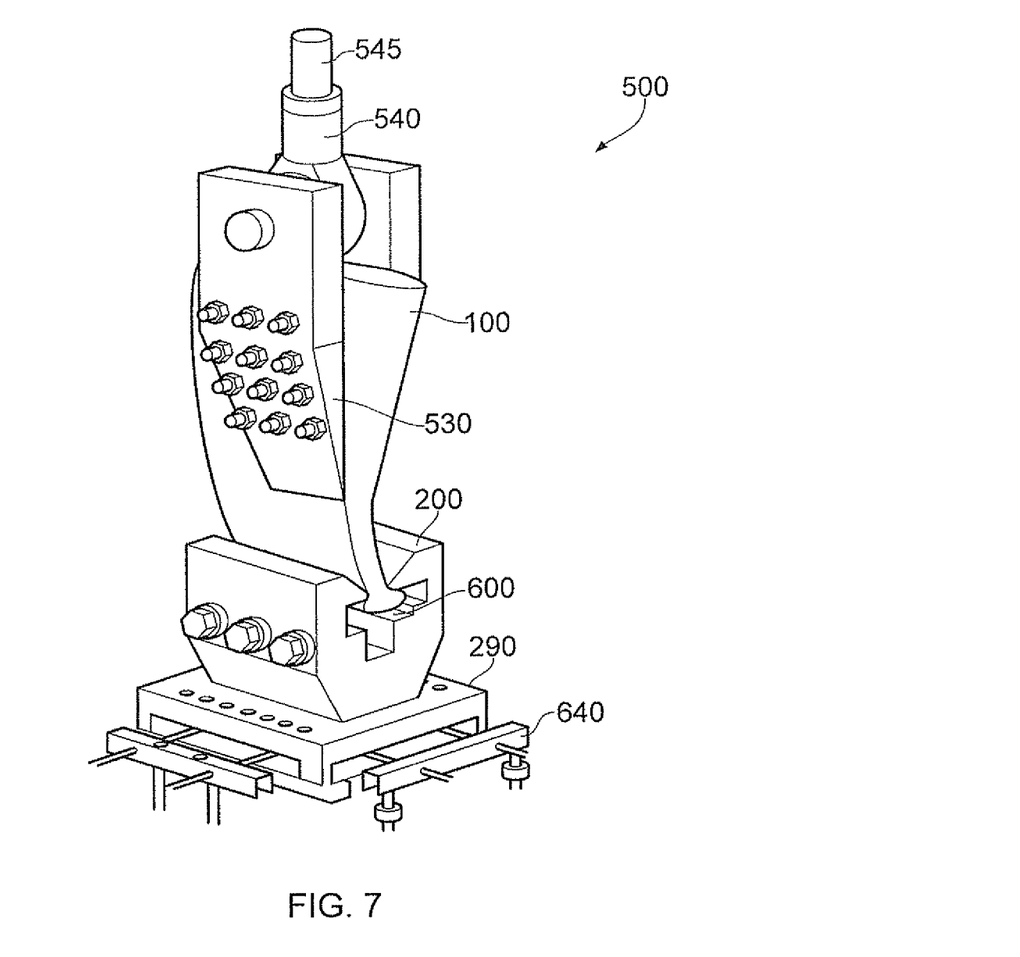
FIG. 7 shows the blade attachment member of FIG. 6 together with a blade specimen, blade mounting member and pre-loading wedge.

FIG. 7 shows blade attachment member 500 together with the blade mounting member 200 and a blade specimen 100 which is held between the two. The blade specimen may include the whole of the aerofoil or, more preferably, a portion thereof. Retaining plates 600 prevent the blade specimen 100 from moving out of the blade mounting member. Meanwhile a wedge 610 is placed in the blade mounting member 200, below the blade specimen in order to push the root 110 of the blade specimen upwards for initial pre-loading which, for example, simulates 10% of the maximum centripetal load. The wedge 610 correctly positions and loads the contact region between the blade specimen root 110 and the mounting member 200 prior to the application of lean and twist and prior to further application of load by the actuator 390.

The wedge 610 may also be used in the arrangement shown in FIGS. 3 to 5. The blade mounting member is attached to a base plate 290 and screw jacks 640 are provided for adjusting the position of the blade mounting member in the x and y directions (i.e. in a plane parallel to the plane of the first structural member 310).

A method of fatigue testing and simulating the life of the blade will now be described. First the regulating members 280 of the blade mounting member 200 are tightened to the required value. Then the blade attachment member 400 is attached to the top of the wing 130 of a blade specimen 100. Then the blade specimen 100 with attached blade attachment member is mounted in the blade mounting member 200. Specifically the root 110 of the blade is inserted into the aperture 210 of the blade mounting member and a pre-loading wedge 610 is used as described as above. The blade mounting member 200 is mounted to the first structural member 310 of the rig 300. A retention system may be used to prevent the blade from walking out of the blade mounting member. The blade attachment member 400 is then fitted to the test rig 300. Specifically, the part for attachment 420 is attached to the block 405 which is attached directly to the test machine actuator 390. The relative position of the blade attachment member 400 and the blade mounting member 200 are adjusted to the correct position to induce the desired blade root and shank stresses. Specifically, the blade mounting member 200 is moved along the base of the rig (i.e. along the first structural member 310) and secured at a location which will give the desired blade lean, twist and off-axis force when the tension load is applied by the actuator 390.

The rig actuator 390 is then used to cyclically load and unload the blade 100 to the desired value. Strain gauges or a pressure/colour contact film may be used to confirm that the contact and shank stresses are representative of the simulated operating conditions (eg those found by full strain gauge engine test results). If this is not the case then the 'disc fixture' and 'load application location' can then be adjusted as required. This loading pattern will be repeated until the desired number of cycles has been reached or the test is considered to have reached the end of its usefulness.

Strain gauges may be monitored throughout the test and loading varied to maintain the correct root and shank conditions.

In this way the root and shank of a blade can be tested for LCF (low cycle fatigue) loading without the need for a whole engine test or spin test. Further, the mounting arrangement and contact region (between root and disc) behaviour is tested without the need for horizontal actuators, as a single vertical actuator 390 can be used. The blade can be loaded in a non axi-symmetric manner and so replicate the lean and twist of the blade, which normally can only be seen on a full gas turbine engine test.

The process is very efficient compared to a conventional LCF spin tests which require a blade set to be accelerated to full velocity and then slowed down. In comparison to a conventional LFC spin test the above apparatus and method increases the test rate from blade set per year, usually comprising of between 20 and 30 blades, to a blade a day thereby reducing the time and cost. Furthermore, additional engine components are not required such as the Annulus Fillers, Support Ring, Fan Disc, Nose Cone and Spinner Fairing are not required in order to represent the correct root and shank loading conditions. Multiple blade root designs and off-optimum loading conditions can be tested for optimisation and proof of concept purposes in a single fixture arrangement. The regulating members allow permit easy alteration of the bulk 'disc feature' displacement and so adapt to any changes in boundary conditions. Easy alteration of the off-axis load position can be achieved by moving the location of the blade mounting member in the test rig; this enables the application to be adapted for any changes in boundary conditions and for fine tuning the contact and shank stresses. Further, contact region chord stress variation can be simulated as well as blade twist and lean.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. An apparatus for simulating stresses experienced by a mounting arrangement of a rotor blade in a rotor disc, the apparatus comprising:
   a mounting member for receiving a blade specimen having a root, said mounting member having an aperture for receiving the root of the blade specimen, and blade contacting regions on either side of said aperture for holding said blade specimen in said aperture;
   and an actuator for applying a tension load to said blade specimen; wherein
   said blade contacting regions are undercut such that there is a gap between said blade contacting regions and a main body of said mounting member, whereby the blade contacting regions are able to deflect outward into said gap when a tension load is applied to said blade specimen.

2. The apparatus of claim 1 together with a blade specimen mounted in the mounting member; said blade specimen having a root.

3. The apparatus of claim 1 wherein said aperture and said gap form a single recess when no blade is mounted in the aperture.

4. The apparatus of claim 1 wherein there are a pair of blade contacting regions each having a respective contact face for contacting the root of a blade specimen, said contact faces being designed to match the profile of the root of the blade specimen.

5. The apparatus of claim 1 having one or more regulating members for regulating stiffness of the mounting member.

6. The apparatus of claim 1 comprising a base for supporting the member and an arrangement for attaching the blade specimen to the actuator.

7. The apparatus of claim 1, wherein the actuator is arranged for cycling the load.

8. The apparatus of claim 1, wherein the apparatus has only a single actuator for applying a load to the blade specimen.

9. A method of simulating stresses experienced by a mounting arrangement of a rotor blade in a rotor disc, comprising the steps of:
   placing a blade specimen having a root in a mounting member for receiving the blade specimen,
   said mounting member having an aperture for receiving the root of the blade specimen, and blade contacting regions on either side of said aperture for holding said blade specimen in said aperture, said blade contacting regions being undercut such that there is a gap between said blade contacting regions and a main body of said mounting member, whereby the blade contacting regions are able to deflect outward into said gap when a tension load is applied to said blade specimen;
   and using an actuator for applying a tension load to said blade specimen.

10. The method of claim 9 further comprising the step of regulating the stiffness of the mounting member by adjusting one or more regulating members.

11. The method of claim 9 wherein the load applied to the blade specimen is cycled.

12. The method of claim 9 wherein only a single actuator is used for applying a load to the blade specimen.

13. An apparatus for simulating the axial and radial stresses experienced by the root and shank of a rotor blade when the rotor blade is in operation; the apparatus comprising:
   a blade mounting member adapted to receive and hold the root of a blade specimen;
   a blade attachment member for attaching to a wing portion of a blade specimen;
   an actuator for applying a force separating the blade mounting member and blade attachment member so as to apply a tension load to a blade specimen when a blade specimen is mounted to the blade mounting member and attached to the blade attachment member; wherein
   one or both of the blade attachment member and blade mounting member is movable relative to the other in a manner such that at least one of a lean and a twist of a blade specimen mounted to the blade mounting member and attached to the blade attachment member is adjustable.

14. The apparatus of claim 13 wherein the apparatus has x, y and z axes, the actuator being arranged for applying a load along the z axis and at least one of the blade attachment member and blade mounting member being movable relative to the other in at least one of the x and y directions.

15. The apparatus of claim 13 wherein the apparatus has first and second opposing structural members, the blade mounting member is mounted directly or indirectly to the first structural member and the blade attachment member is supported by the second structural member, the blade mounting member being movable in a plane substantially parallel to the plane of the first structural member.

16. The apparatus of claim 15 wherein the blade mounting member is mounted to the first structural member on one or more rails or recesses and movable along said rails or recesses.

17. The apparatus of claim 15 wherein the actuator is mounted to the second structural member and wherein a blade receiving part of the blade mounting member is offset along at least one of the x and y axis relative to the actuator.

18. The apparatus of claim 13 wherein the blade mounting member has an aperture for receiving the root of the blade, and blade contacting regions on either side of said aperture for holding said blade specimen in said aperture; wherein said blade contacting regions are undercut such that there is a gap between said blade contacting regions and a main body of said blade mounting member, whereby the blade contacting regions are able to deflect outward into said gap when a tension load is applied to said blade specimen.

19. The apparatus of claim 13 wherein a link between the blade attachment member and the actuator has a degree of play to allow non axi-symmetric loading.

20. The apparatus of claim 13 wherein the blade attachment member is provided with a part for attachment to the actuator and the position of said part can be adjusted in order to fine tune its position in relation to a central axis of the blade attachment member.

21. A method of simulating the axial and radial stresses experienced by the root and shank of a rotor blade when the rotor blade is in operation; the method comprising the steps of:
  providing a blade mounting member adapted to receive and hold the root of a blade specimen;
  providing a blade attachment member which is adapted for attachment to the wing of a blade specimen;
  mounting the root of a blade specimen in the blade mounting member and attaching a wing of the blade specimen to the blade attachment member;
  adjusting the relative positioning of the blade mounting member and the blade attachment member in order to achieve a desired lean and twist of said blade specimen,
  and using an actuator to apply a force to at least one of a first and second structural member so as to apply a tension load to said blade specimen.

22. The method of claim 21 further comprising the step of checking strain indicators applied to at least one of the blade specimen and the blade mounting member to confirm that stresses are at the desired level.

23. The method of claim 21 further comprising the step of adjusting the load until a desired strain is achieved.

24. The method of claim 21 further comprising the step of cycling the load applied to the blade.

25. The method of claim 21 wherein axial and radial stresses are applied to the root of the blade specimen by a single actuator.

* * * * *